(12) United States Patent
Hermanson et al.

(10) Patent No.: US 9,462,835 B1
(45) Date of Patent: Oct. 11, 2016

(54) ELBOW PAD

(75) Inventors: Jon Hermanson, Knoxville, TN (US); Bill Ott, Knoxville, TN (US)

(73) Assignee: ALBAHEALTH LLC, Rockwood, TN (US)

( * ) Notice: Subject to any disclaimer, the term of this patent is extended or adjusted under 35 U.S.C. 154(b) by 1077 days.

(21) Appl. No.: 13/039,021

(22) Filed: Mar. 2, 2011

(51) Int. Cl.
*A41D 13/08* (2006.01)
*A41D 13/05* (2006.01)

(52) U.S. Cl.
CPC .............. *A41D 13/08* (2013.01); *A41D 13/05* (2013.01)

(58) Field of Classification Search
CPC ....... A41D 13/08; A63B 71/08; A63B 71/14
USPC ... 2/16, 18, 19, 20, 158, 159, 161 R, 161 A, 2/162, 167, 168, 2, 170; 128/77, 87 R
See application file for complete search history.

(56) References Cited

U.S. PATENT DOCUMENTS

| | | | |
|---|---|---|---|
| 1,351,731 A * | 9/1920 | Baldwin | 2/16 |
| 3,259,910 A * | 7/1966 | Daignault | 2/24 |
| 3,446,880 A * | 5/1969 | Enicks | 264/46.6 |
| 3,888,244 A * | 6/1975 | Lebold | 602/4 |
| 3,911,497 A * | 10/1975 | Lewis et al. | 2/16 |
| 4,041,940 A * | 8/1977 | Frankel et al. | 602/26 |
| 4,190,902 A * | 3/1980 | Rhee | 2/16 |
| 4,484,361 A | 11/1984 | Leighton et al. | |
| D327,961 S | 7/1992 | Decker | |
| 5,222,256 A | 6/1993 | Wang | |
| D341,005 S | 11/1993 | Pratt | |
| D346,245 S | 4/1994 | Krent et al. | |
| D364,009 S | 11/1995 | Engdahl | |
| 5,594,954 A | 1/1997 | Huang | |
| 5,716,120 A | 2/1998 | Hung | |
| D396,330 S | 7/1998 | Oetting | |
| 5,887,277 A | 3/1999 | Lohman | |
| D417,036 S | 11/1999 | Hamowy | |
| D430,362 S | 8/2000 | Pagotto | |
| 6,205,583 B1 | 3/2001 | Beland | |
| D440,017 S | 4/2001 | Pagotto | |
| 7,356,849 B2 | 4/2008 | Morrow et al. | |
| D594,161 S | 6/2009 | Worden | |
| 2008/0132822 A1* | 6/2008 | Hermanson et al. | 602/63 |
| 2010/0083415 A1* | 4/2010 | Beckford | 2/16 |
| 2010/0113996 A1* | 5/2010 | Batz et al. | 602/20 |
| 2010/0160842 A1* | 6/2010 | Wickstrom | 602/4 |
| 2010/0212485 A1* | 8/2010 | Carter | 89/36.02 |
| 2010/0268135 A1* | 10/2010 | Summit et al. | 602/12 |
| 2010/0312160 A1* | 12/2010 | Creighton et al. | 602/62 |
| 2011/0167529 A1* | 7/2011 | Anderson et al. | 2/2.5 |
| 2011/0201982 A1* | 8/2011 | Thompson | 602/3 |
| 2012/0004586 A1* | 1/2012 | Martino | 602/20 |

* cited by examiner

*Primary Examiner* — Bobby Muramoto, Jr.
(74) *Attorney, Agent, or Firm* — Baker, Donelson, Bearman, Caldwell & Berkowitz, PC; Dorian Kennedy

(57) ABSTRACT

An elbow pad (10) is disclosed having a padding member (11), a forward strap (12), and forward strap retainer (14), a midway strap (16), and a midway strap retainer (17). The padding member has a central floor (23), a first trapezoidal side wall (24), a second trapezoidal side wall (25), and a generally rectangular, triple layered end wall (26) to protect the posterior side of the elbow. The elbow pad extends from the elbow to the wrist of a wearer to protect the entire forearm.

9 Claims, 2 Drawing Sheets

ELBOW PAD

TECHNICAL FIELD

This invention relates generally to a protector and more specifically to an elbow or arm pad.

BACKGROUND OF THE INVENTION

People oftentimes harm one's elbow resulting in an injury that must be protected from further harm due to subsequent contact. Also, people with physical disabilities limiting arm movement may develop sensitive, calloused, or worn areas on the elbow and forearm areas from continuous contact with wheelchair armrests, feeding trays, beds or the like. Lastly, the skin of the elderly typically become susceptible to bruising and shearing during normal daily activity, especially in the area of the elbow and forearm. For these people and others, the medical field has produced elbow pads or protectors which cushion the elbow joints.

To date, the protectors which have been used in the medical industry have been relatively soft foam pads that are strapped to the injured elbow of a person. These pads have not proven to provide adequate protection of the forearms in a comfortable manner.

Accordingly, it is seen that a need remains for an elbow pad that protects a person's elbow and adjacent area while remaining comfortable to the wearer. It is to the provision of such therefore that the present invention is primarily directed.

SUMMARY OF THE INVENTION

In a preferred form of the invention an elbow pad for a human arm having an elbow and a wrist comprises a padding member having a central floor, a first side wall, a second side wall, and an end wall. The end wall comprises a first portion integrally extending from the first side wall, a second portion integrally extending from the second side wall, and a third portion integrally extending from the floor. The first, second and third portion are joined together. The elbow pad also has a first elongated strap extending between the padding member first side wall and the padding member second side wall.

DETAILED DESCRIPTION

Figure 1:
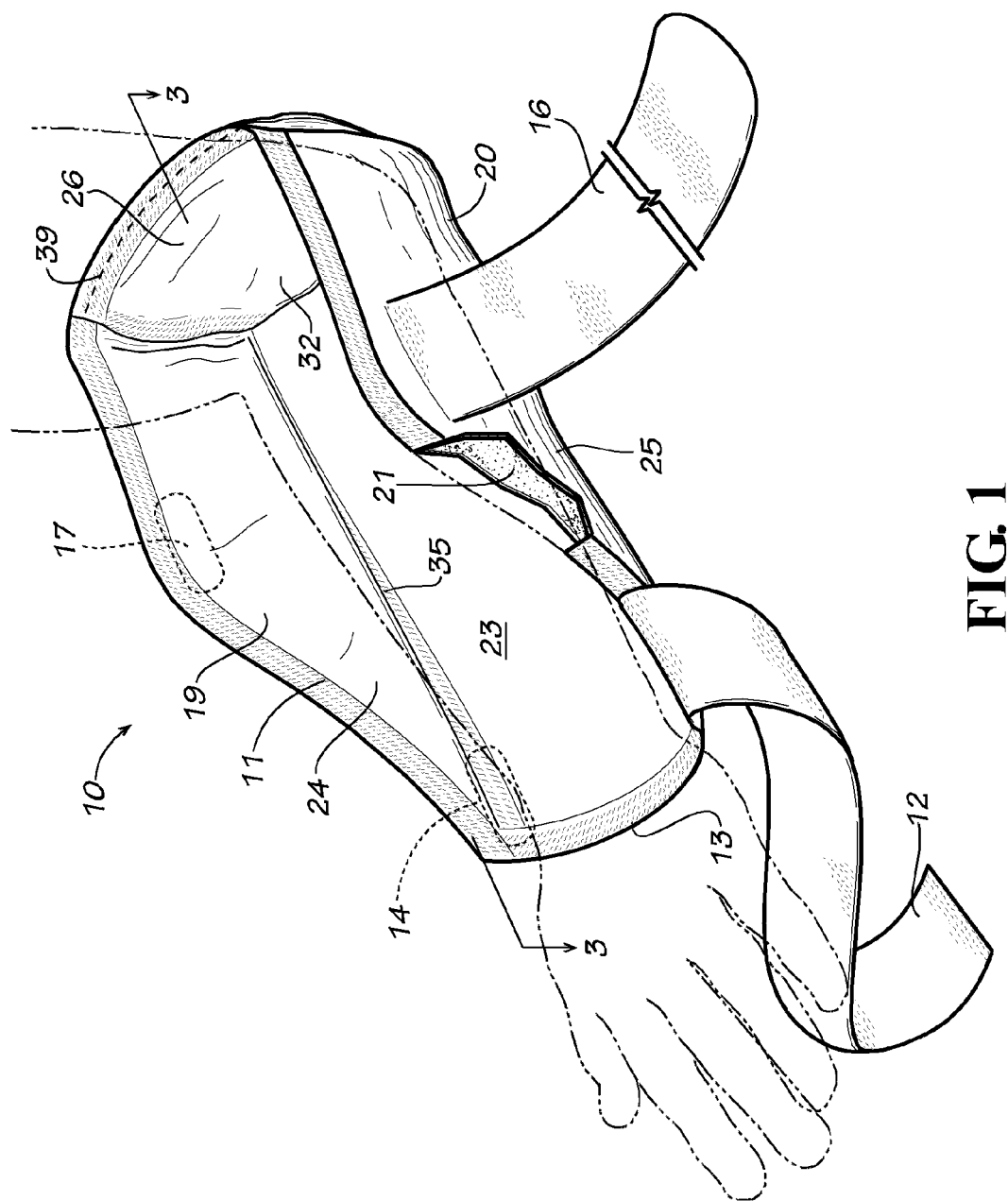
FIG. 1 is a perspective view of a preferred form of the elbow pad in a preferred form of the invention, shown with a portion of an arm.
Figure 2:
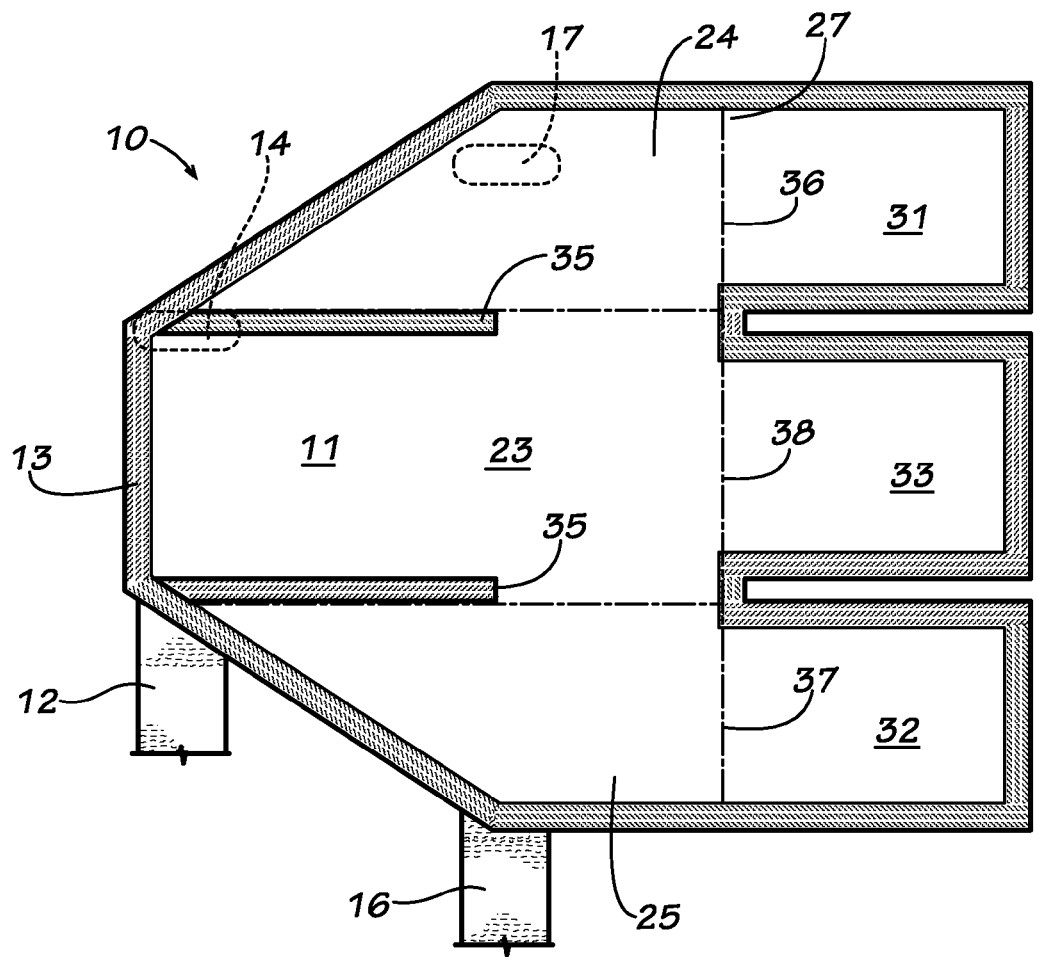
FIG. 2 is a top plan view of the unassembled elbow pad of FIG. 1.

With reference next to the drawings, there is shown an elbow pad 10 in a preferred form of the invention. The elbow pad 10 includes a padding member 11, a forward strap 12 positioned adjacent a front end 13 of the elbow pad, and forward strap retainer 14, a midway strap 16, and a midway strap retainer 17. The padding member 11 is made of a three-ply or three-layered material having an inwardly facing outer covering layer 19, an outwardly facing outer covering layer 20, and an inner batting layer 21 sandwiched between the two outer covering layers 19 and 20. The outer covering layers 19 and 20 may be made of a 45 GSM (grams per square meter) spun lace polyester. The inner batting layer 21 may be made of a 245 GSM polyester fiber. The straps 12 and 16 may be made of non-woven polyester having loops or loose fibers within the material, sometimes referred to as a polyester felt. The forward and midway strap retainers 14 and 17 are made of a releasable hook-type fastener which releasably mates with the loops or fibers of straps 12 and 16.

Figure 3:
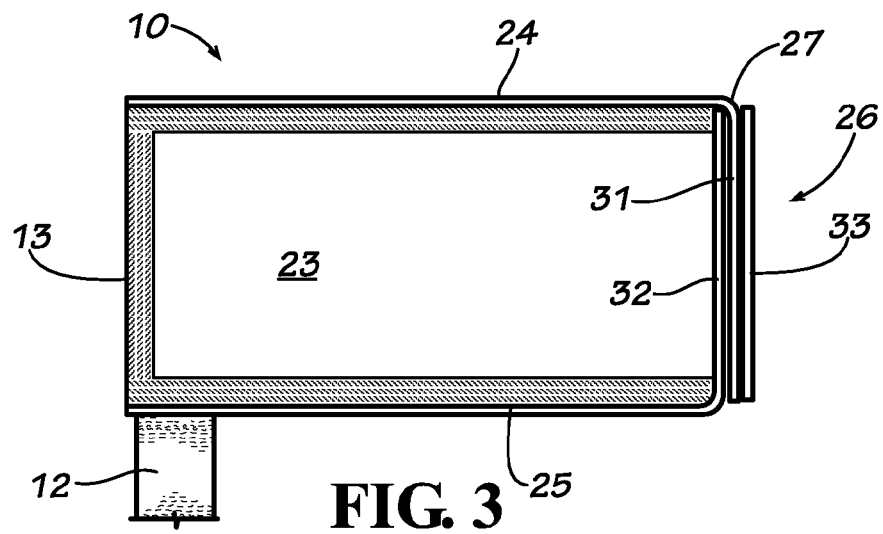
FIG. 3 is a cross-sectional view of the elbow pad of FIG. 1.

The padding member 11 has a central floor 23, a first trapezoidal side wall 24, a second trapezoidal side wall 25 oppositely positioned from the first trapezoidal side wall 24, and a generally rectangular, triple thick or layered end wall 26 positioned opposite front end 13 and between the rearward ends 27 of the side walls 24 and 25. As best shown in FIG. 3, the triple layered end wall 26 is formed from a first rectangular portion 31 integrally extending from the rearward end 27 of the first trapezoidal side wall 24, a second rectangular portion 32 integrally extending from the rearward end 27 of the second trapezoidal side wall 25, and a third rectangular portion 33 integrally extending from the rearward end 27 of the central floor 23. The term integrally extending from is intended to describe that the portion extends from and continues uninterrupted from the side wall and is not merely a separate piece of material which is then joined to the side wall.

During the manufacturing process of the padding member 11, the side walls 24 and 25 are rotated about seam lines 35 to an upright position generally normal to the central floor 23. The first and second rectangular portions 31 and 32 are then folded along fold lines 36 and 37 to a position generally normal to their co-extensive trapezoidal side walls 24 and 25 from which they extend, and the third rectangular portion 33 is folded along fold line 38 to an upright position generally normal to the central floor 23. The top edges of the first, second and third rectangular portions are then joined together, as with a stitching 39. As such, the triple layered end wall 26 is formed from the overlying first, second and third rectangular portions 31, 32 and 33. The seam line 35 may be formed by heating the material while under pressure, as for example by conventional sonic welding and rolling. It should also be understood that all edges of the material are likewise formed with seam lines 41 along the margin in the same manner to ensure that the edges of the material layers do not separate from each other and to form a clean edge. The seaming of the pad allows it to be formed into a L-shaped bowl so as to protect an elbow residing within the "bowl". The first, second and third rectangular portions may be bonded, coupled or joined together in any conventionally know manner, such as with the aforementioned stitching, or alternatively with an adhesive, heat, pressure or combination thereof.

In use, the elbow of a person is positioned within the "bowl" of the elbow pad 10 so that the posterior side of the elbow is adjacent the end wall 26 and the forearm rests upon the central floor 23. Preferably, the elbow pad 10 is sized so that the front end 13 of the elbow pad 10 is positioned in the vicinity immediately adjacent or directly below the person's wrist, thereby allowing virtually the entire forearm of a person to be covered and therefore protected by the elbow pad. As used herein, the forearm is defined as the portion of the arm extending from and including the elbow to the wrist. It should be understood that even with the elbow residing within the "bowl" of the elbow pad, the arm may be moved between a bent position and a straight position because of the pliability of the pad material, i.e., the pad material bends thereby allowing relative movement of the arm.

The inwardly facing outer covering layer 19 provides a soft feel for the person while also allowing bodily fluids to pass through the outer covering layer 19 (fluid permeable) so as to be absorbed by the inner batting material 21. The outwardly facing outer layer 20 allows for easy sliding movement of the elbow pad upon an underlying surface.

It should be understood that the triple layering of the end wall 26 provides the greatest protection to the area of the arm which is most vulnerable to being hit against an object.

It thus is seen that an elbow pad is now provided that allows for greater comfort while protecting both the elbow and the forearm of a wearer. Although the protector has been illustrated and described in its preferred form, it should be understood that many modifications, additions and deletions may be made to that specific form without departure from the spirit and scope of the invention as set forth in the following claims.

The invention claimed is:

1. An elbow pad for a human arm having an elbow and a wrist, the elbow pad comprising:
    a padding member having a central floor, a first side wall, a second side wall, and an end wall, said end wall includes three overlaying portions which include a first portion integrally extending from said first side wall, a second portion integrally extending from said second side wall, and a third portion integrally extending from said floor, said first, second and third portion being joined together, and
    a first elongated strap extending between said padding member first side wall and said padding member second side wall.

2. The elbow pad of claim 1 further comprising a second elongated strap extending between said padding member first side wall and said padding member second side wall.

3. The elbow pad of claim 1 wherein said padding member comprises a first outer covering layer, a second outer covering layer, and an inner padding layer positioned between said first and second outer covering layers.

4. The elbow pad of claim 3 wherein said first outer covering layer is fluid permeable and said inner padding layer is fluid absorbent.

5. The elbow pad of claim 1 wherein said padding member is sized to extend from an anterior portion of the wearer's elbow to the wearer's wrist.

6. An elbow pad for a human arm, the elbow pad comprising:
    a padding member having a central floor, a first side wall having a main portion integrally extending from said central floor and an end portion extending from said first side wall main portion but separate from said central floor, a second side wall having a main portion integrally extending from said central floor and an end portion extending from said second side wall main portion but separate from said central floor, and an end wall integrally extending from said central floor, said first side wall end portion, said second side wall end portion and said end wall overlaying each other said central floor being configured to overlie the entire forearm of a wearer, and
    a first elongated strap extending between said padding member first side wall and said padding member second side wall.

7. The elbow pad of claim 6 further comprising a second elongated strap extending between said padding member first side wall and said padding member second side wall.

8. The elbow pad of claim 6 wherein said padding member comprises a first outer covering layer, a second outer covering layer, and an inner padding layer positioned between said first and second outer covering layers.

9. The elbow pad of claim 8 wherein said first outer covering layer is fluid permeable and said inner padding layer is fluid absorbent.

* * * * *